United States Patent
Schiffrin et al.

(10) Patent No.: US 7,230,078 B2
(45) Date of Patent: Jun. 12, 2007

(54) SOLUBLE TOLL-LIKE RECEPTOR

(75) Inventors: Eduardo Schiffrin, Crissier (CH); Michael Affolter, Savigny (CH); Mario Labeta, Cardiff (GB)

(73) Assignee: Nestec S.A., Vevey (CH)

( * ) Notice: Subject to any disclaimer, the term of this patent is extended or adjusted under 35 U.S.C. 154(b) by 310 days.

(21) Appl. No.: 10/489,553

(22) PCT Filed: Sep. 13, 2002

(86) PCT No.: PCT/EP02/10410

§ 371 (c)(1),
(2), (4) Date: Mar. 11, 2004

(87) PCT Pub. No.: WO03/025015

PCT Pub. Date: Mar. 27, 2003

(65) Prior Publication Data

US 2005/0124538 A1  Jun. 9, 2005

(30) Foreign Application Priority Data

Sep. 17, 2001 (EP) ................................ 01121698

(51) Int. Cl.
*C07K 14/47* (2006.01)
*C12N 15/12* (2006.01)
*A61K 38/00* (2006.01)

(52) U.S. Cl. ................... 530/350; 435/69.1; 435/71.1; 435/320.1; 536/23.5; 514/2

(58) Field of Classification Search .................... None
See application file for complete search history.

(56) References Cited

U.S. PATENT DOCUMENTS 5,744,145 A  4/1998  Bertoli et al. ............... 424/401

FOREIGN PATENT DOCUMENTS

| EP | 0 864 585 A1 | 9/1998 |
|---|---|---|
| WO | WO 99/37772 | 7/1999 |
| WO | WO 0024776 | 5/2000 |
| WO | WO 0075358 | 12/2000 |

OTHER PUBLICATIONS

James A. Wells, Sep. 18, 1990, Biochemistry, vol. 29, No. 37, pp. 8509-8517.*
Iwaki et al. The Journal of Biological Chemistry, vol. 277, No. 27, pp. 24315-24320, Jul. 2002.*
LeBouder et al, Journal of Immunology, 2003, vol. 171, pagers 6680-6689.*
Flo et al. article entitled "Detection of Soluble TLR2 In Human Serum Samples by Elisa" *NTNU, Institute of Cancer Research and Molecular Biology*, Trondheim, Norway, 1 page.
Labéta et al. article entitled "Innate Recognition of Bacteria in Human Milk Is Mediated by a Milk-Derived Highly Expressed Pattern Recognition Receptor, Soluble CD14" *J. Exp. Med.*, vol. 191, No. 10, May 15, 2000, pp. 1807-1812.
Filipp et al. article entitled "Soluble CD14 Enriched in Colostrum and Milk Induces B Cell Growth and Differentiation" *PNAS*, vol. 98, No. 2, Jan. 16, 2001, pp. 603-608.
Du et al. article entitled "Analysis of Tlr4-Medicated LPS Signal Transduction in Macrophages by Mutational Modification of the Receptor" *Blood Cells, Molecules, and Diseases* (1999 25(6) Nov. 15, 1999, pp. 328-338.
Xu et al. article entitled "Structural Basis for Signal Transduction by the Toll/Interleukin-1 Receptor Domains" *Nature*, vol. 408, Nov. 2, 2000, pp. 111-115.
Pruitt et al. article entitled "Increased Soluble Interleukin-1 Type II Receptor Concentrations in Postoperative Patients and in Patients With Sepsis Syndrome" *Blood*, vol. 87, No. 8, Apr. 15, 1996, pp. 3282-3288.
O'Neill et al. article entitled "The IL-I Receptor/Toll-Like Receptor Superfamily: Crucial Receptors for Inflammation and Host Defense" *Trends, Immunology Today*, May 2000, vol. 21, No. 5, pp. 206-209.
Mantovani et al. article entitled "Decoy Receptors: A Strategy to Regulate Inflammatory Cytokines and Chemokines" *Trends in Immunology*, vol. 22, No. 6, Jun. 2001, pp. 328-336.
Kolb article entitled "The Prospects of Modifying the Antimicrobial Properties of Milk" *Biotechnology Advances*, vol. 19, 2001, pp. 299-316.
Medzhitov R, Janeway CA Jr., article entitled "Innate Immunity: The Virtues of a Nonclonal System of Recognition", CELL, vol. 91, pp. 295-298 (Oct. 31, 1997).
Imgenex, www.imgenex.com, website entitled: "Polyclonal Antibody to TLR2 (Toll-like Receptor 2)", commercialized by Biocarta Europe GmbH, (Oct. 4, 2004).
Santa Cruz Biotechnology, Inc., www.scbt.com, website entitled: "TLR2 (N-17): sc-8689", Apr. 2001.
Sambrook et al., *Molecular Cloning, A Laboratory Manual*, Cold Spring Harbor Press, Ch. 16-17, pp. 16.1-17.44 (1989).
D. Lipman et al., article entitled: "Basic Local Alignment Search Tool", J. Mol. Biol., vol. 215, pp. 403-410 (1990), Altschul et al.
Altschul, S.F., et al., article entitled: "Gapped BLAST and PSI-BLAST: A New Generation of Protein Database Search Programs", Nucleic Acids Res., vol. 25, pp. 3389-3402 (1997).
Smith, T.F. and Waterman, M.S., article entitled: "Pattern Recognition in Genetic Sequences by Mismatch Density", Bull. Math. Biol., vol. 46, pp. 501-514 (1994), Sellers, Pecker.

(Continued)

Primary Examiner—Prema Mertz
Assistant Examiner—Fozia Hamud
(74) Attorney, Agent, or Firm—Bell, Boyd & Lloyd LLP

(57) ABSTRACT

A novel, soluble protein similar to the known Toll-like receptor (TLR) family is disclosed. The present invention relates to these new soluble polypeptides, to nucleotide sequences encoding the polypeptides, to antibodies selectively binding to the polypeptide and to expression systems suitable for producing the polypeptide. The polypeptide is useful for modulating inflammatory reactions in mammals that include the actions of TLR.

5 Claims, 3 Drawing Sheets

OTHER PUBLICATIONS

Durieux, J.J., et al., article entitled: "The Two Soluble Forms of the Lipopolysaccharide Receptor, CD14: Characterization and Release by Normal Human Monocytes", Eur. J. Immunol., vol. 24, pp. 2006-2012 (1994).

J. Coligan et al, "Electroblotting from Playacrylamide Gels" *Current Protocols in Protein Science*, J. Wiley & Sons, Ch. 10, Sec. 10.7 (1995).

J. Coligan et al, "In-Gel Digestion of Proteins for MALDI-MS Fingerprint Mapping" *Current Protocols in Protein Science*, J. Wiley & Sons, Ch. 16, Suppl. 14, Sec. 4 (1998), Jimencz et al.

Frey E.A., et al., article entitled: "Soluble CD14 Participates in the Response of Cells to Lipopolysaccharide", J. Exp. Med., vol. 176, pp. 1665-1671 ( Dec. 1992).

* cited by examiner

US 7,230,078 B2

SOLUBLE TOLL-LIKE RECEPTOR

FIELD OF INVENTION

The present invention pertains to the field of modulation and regulation of immune responses of vertebrates. In particularly, it reports a novel polypeptide isolated from milk, which is denominated soluble Toll-like receptor regulatory molecule (sTLRR). The present invention also relates to a nucleic acid molecule encoding the novel polypeptide, to a consumable product, a pet food and a cream or lotion comprising the polypeptide.

BACKGROUND OF THE INVENTION

The sterile fetal intestine is abruptly colonised by environemental microbes immediately after birth. The main bacterial components early during colonisation are Gram-negative, endotoxin (LPS) producing bacteria. They may contribute to a number of infectious and inflammatory conditions of the newborn gastrointestinal tract. It has been demonstrated that breast-fed newborns have a lower incidence of intestinal infections, intestinal inflammatory conditions, lower incidence of respiratory infections, and, later in life, less allergic diseases. A number of human milk components may explain the protective role, among, others, immunocompetent cells, antibodies transfering pasive immune protection, human milk oligosaccharides, lysozyme, lactoferrin and other factors have been evoked.

Toll receptors, mediating cell signalling in Drosophila, have to be seen in a completely different context. This important family of trans-membrane molecules is primarily involved in morphogenesis, but later in the life of the adult fly its activation induces a defensive response during infections.

The mammalian homologues of the Toll receptor family were discovered recently (Medzhitov R, Janeway C A Jr. Innate immunity: the virtues of a nonclonal system of recognition, Cell (1997) 91: 295-298). Owing to the apparent relationship, the mammalian homologues are called Toll-like receptors (TLR). As Toll and Toll related proteins in the fly, TLR are transmembrane cell-surface proteins that extend into the intracellular domain. The extracellular region (N-terminal end) generally contains multiple leucine-rich repeats (LRR), and, in the known human and Drosophila family members, a top Cys-rich module that presumably is a juxtamembrane spacer. The intracellular (C-terminal end) domains of the mammalian TLR and Drosophila Toll proteins are similar to the one of the well-described Interleukin 1 and 18 receptors (IL-1R and IL-18R), which indicates similar mechanisms and participants of downstrem signal transducing. So far a family of about ten mammalian TLRs has been identified.

A lot of research has since been conducted in order to find potential ligands that could activate the TLR-mediated signalling from the extracellular side, and, to determine the intracellular signalling pathway of the activated receptor.

It has become clear that the TLR family members are part of the mammalian innate immune system responsible for recognition of and response to bacteria and bacterial cell wall components.

WO 0075358 is based on the discovery of novel TOLL family members (TOLL nucleic acid family members). It is thought that the TOLL molecules according to the invention are useful as targets for developing modulating agents. Hence, nucleotide and amino acid sequences are disclosed and claimed. FIG. 1 of WO 0075358 shows the nucleotide sequence of the human TOLL protein as well as the amino acid sequence encoded therewith. This TOLL protein may be membrane proteins, which function as receptors, and they may be involved in immune signalling mechanisms.

WO 0024776 discloses a novel molecular species TLR6 which belongs to the Toll family. Hence, TLR6 regulates the expression of various genes participating in immune response. Also a gene encoding the receptor is given.

Besides the scientific research, no technically exploitable effect and no other functioning that the ones described above has been disclosed so far.

Consequently, a problem of the present invention is to provide a means of administering an active substance to an individual, whereby the substance will regulate the activatory pathways induced by bacterial products as mediated through components of TLRs, and more specifically TLR-2.

SUMMARY OF THE INVENTION

Consequently, in a first aspect the present invention provides an isolated polypeptide according to claim 1, which is identified by any of SEQ ID. Nos. 1 or 2, or variants and fragments thereof, obtainable by deleting, adding or substituting one or more amino acids, which have a degree of homology to the polypeptide of any of SEQ ID. Nos. 1 or 2 of at least 90% and are functional, soluble polypeptides.

In second aspect, the present invention provides an antibody that selectively binds to the polypeptide according to the invention.

In a third aspect, the present invention provides an isolated nucleic acid molecule having a nucleotide sequence encoding the polypeptide according to the invention.

In a fourth aspect, the present invention provides a consumable product comprising the polypeptide according to the present invention.

In a fifth aspect, the present invention provides a cream, lotion or unguent comprising the polypeptide according to the invention.

In a further aspect, the present invention provides a method for prophylaxis, prevention, treatment or therapy of inflammatory conditions or allergic reactions in a mammal, comprising administering an effective amount of the polypeptide according to the invention.

DETAILED DESCRIPTION OF INVENTION

Figure 1:
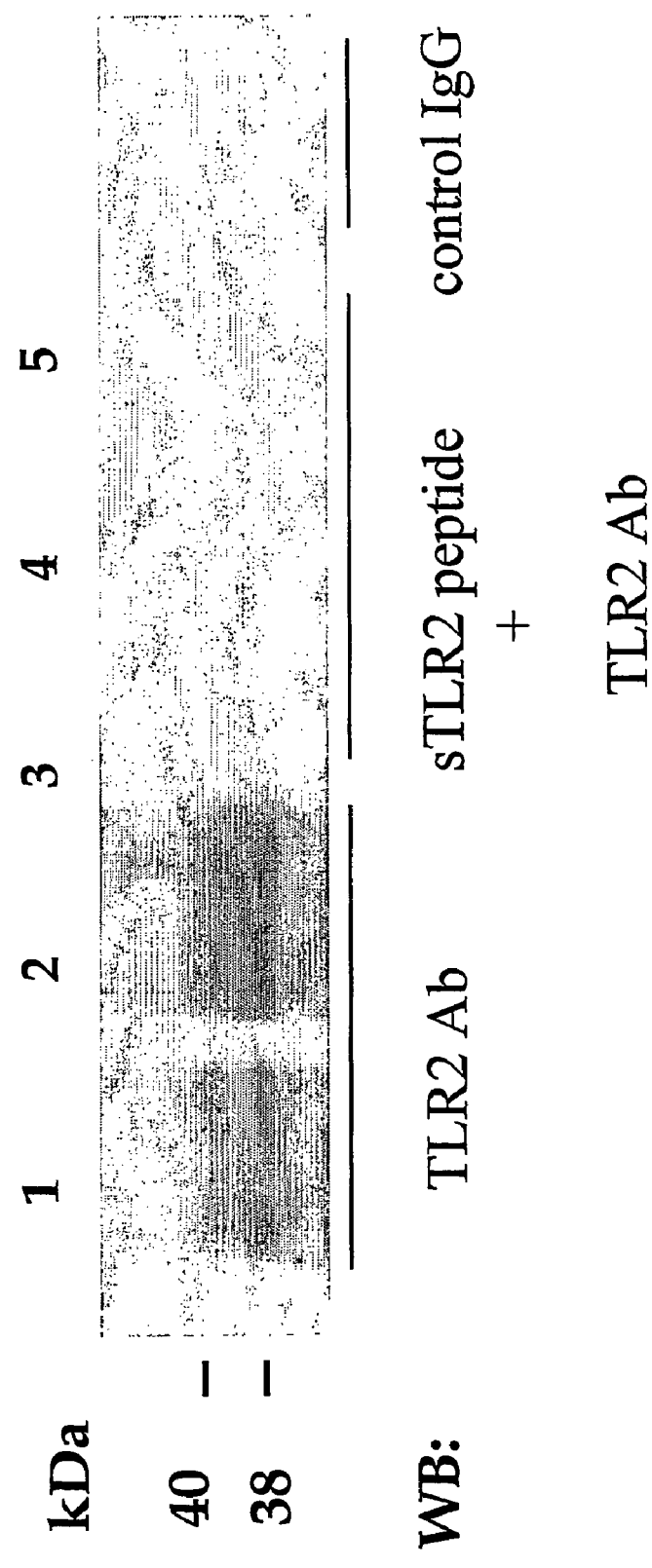
FIG. 1 shows a Western blot analysis of human milk fractions under reducing conditions using 10% SDS-gel. Bands of sTLRR were revealed using the anti-TLR-2 polyclonal antibody (TLR2 Ab, lanes 1 and 2). The anti TLR-2 antibody was also incubated, before blotting, with the peptide used to raise the antibody (TLR2 peptide, see lanes 3 and 4). Also a different antibody was tested (IgG) as isotype control (lane 5).

The present invention is based on the surprising discovery of a molecular component of human breast milk, which shows high homology with the extracellular domain of TLRs molecules, and more specifically with TLR-2. This milk component thus constitutes a naturally occurring soluble derivative of the human TLR2. It is particularly surprising that a soluble variant of a protein known as a transmembrane protein was found in human milk. The present invention is, additionally, based on the possibility that the soluble Toll-like receptor regulatory molecule (hereafter sTLRR) in milk by its interactions with putative TLR-2 ligands, i.e. lipoproteins of Gram-positive bacteria, LPS, sCD14. These play a crucial role in the regulation of immune responses of mammals, especially of immune responses against bacterial conserved molecules present in the intestinal tracts of mammals. Therefore we designate this molecule as soluble toll-like receptor regulatory molecule or soluble Toll-like receptor.

An advantage of the polypeptide according to the present invention is that it provides a tool for regulating inflammatory reactions of a mammal against an antigen.

Another advantage of the present invention is that it provides a polypeptide that is effective in inhibiting, downregulating or preventing inflammatory reactions in a mammal.

Yet another advantage of the present invention is that it provides a polypeptide that is useful as medicament or a cosmetic.

Yet another advantage of the present invention is that it is particularly suitable for prophylaxis, prevention or therapy of gastro-intestinal inflammations.

Within the context of this specification the word "comprises" is taken to mean "includes, among other things". It is not intended to be construed as "consists of only".

Within the context of this specification the word "a homologue of TLR" or "related to TLR" is taken to mean proteins that are recognised by antibodies that specifically bind to any known TLR. More specifically, antibodies that bind to a region within the ectodomain of any known TLR. Since it is expected that novel family members of TLR will be found in humans as well as in other organisms the definition also is intended to include proteins that are recognised by antibodies that are directed to these novel TLR proteins.

Within the context of the present invention, the term "activity" is not intended to be restricted to enzymatical activity. However, it is intended to also refer to the function of binding a ligand or a group of ligands that themselves may also be bound together. Hence, all functions that sTLRR may fulfill are encompassed in the term "activity".

The term "effective" refers to the state of a molecule, for example a peptide, in which it performs the functions it normally performs under in vivo conditions.

In the context of the present invention, the term "soluble" refers to polypeptides, which are soluble in their effective form and under the circumstances of their natural function. Hence, they are soluble at a pH that corresponds, for example, the pH of human breast milk.

Within the context of the present invention, the term "sTLRR", being an abbreviation of "soluble Toll-like receptor regulatoy molecule" is intended to encompass any polypeptide according to the present invention. For reasons of economy and space the term sTLRR is sometimes used, also because it is thought to be the most appropriate denomination, reflecting its relationship and/or its ability to be recognized by anti-TLR antibodies and because it is soluble.

Within the context of the present invention, the term "soluble Toll like receptor regulatory molecule" (sTLRR) is intended to mean that the novel polypeptide can be detected in any cell-free preparation of biological fluids, including but not limited to, human milk and plasma. Any purified or semipurified form of this polypeptide obtained from the sources mentioned previously shows the activity documented by this invention. For example, sTLRR may be found in other body fluids than milk, as blood, or in milk of other mammals than humans as goat, sheep, cow, for example.

Within the context of the present invention, the term "mutation" is intended to include all known kinds of alterations in a nucleotide sequence. It is not intended to only include point mutations, but for example also deletion, insertion, frame shift, nonsense, missense mutations.

Within the context of the present invention, the term "homology" or "homologue", as encompassing homologues of an amino acid sequence is to be understood as to mean "having a common evolutionary origin". This is often used together with the term "similarity", which referes to comparisons of a sequence with another sequence and which may help to determine homology. Models for determining homology are given below.

The term "functional food ingredient" is intended to refer to a substance that, albeit bioactive, is not a medicament. Medicaments usually contain active principles that must be admitted or allowed for use as a medicament by governmental authorities, because their consumption may exhibit undesired side effects. Functional food ingredients, on the other hand, usually reflect active principles beyond a strictly nutritional purpose that are known not to be deleterious to a consumer, mainly because they naturally occur in food, such as milk, for example.

The polypeptide according to the present invention may have a degree of homology to the polypeptide as identified by any of SEQ ID. Nos. 1 or 2 of at least 95%, preferably at least 98%, for example.

The polypeptide according to the present invention may have the sequence as identified by SEQ. ID. No. 1 or 2.

In an embodiment of the present invention, the polypeptide has a molecular size of about 22, 25, 38, 40, 60, 70 and/or 80 kDa in its effective form.

These molecular weights of the polypeptides, however, refer to glycosylated peptides, which affects the weight. The 80 kDa "full length" extracellular, soluble part of human TLR-2 (sTLRR), according to the present invention, for example, would be only 64.4 kD without glycosylation. It is mentioned that human sTLRR has 4 potential N-glycosylation sites (-Asn-Xaa-Ser/Thr-) and bovine has three of them (human: Asn96, Asn181, Asn396, Asn424; bovine: Asn94, Asn178, Asn422).

In a further embodiment, the polypeptide of the present invention is a homologue of or related to the Toll-like receptor (TLR)-family and is soluble in its effective form.

Hence, the polypeptide according to the present invention may be characterised by its ability to compete with TLR for the same ligand or the same group of ligands.

In another embodiment, the polypeptide according to the present invention is obtainable by immunoprecipitation of mammalian fluids such as breast milk serum, plasma or intestinal content, conducted with an anti TLR antibody, for example.

The sTLRR of the present invention may be obtained from human milk, especially during the early stages of lactation. Apparently, the sTLRR interacts with or binds to other proteins or molecules present in milk or from exterior sources. The size of the polypeptide as measured on a SDS gel may be variable, depending on the cofactors/molecules bound to it.

A possible and easy technique of isolating the protein is the affinity chromatography, also called immunochromatography. This method, which is well known to the skilled person, exploits the specific binding of a protein against a specific antibody. An anti-TLR antibody (e.g. an anti-TLR 2 antibody) is held on a solid matrix. The antibody may be covalently bound to the matrix, exposing its variable and specific part. The matrix may consist of chemically inert beads to which the antibody is attached. The beads bound to the antibody are loaded in a column. When a liquid comprising sTLRR (e.g. human milk or serum) is rinsed through the column, the polypeptide will be bound to the antibody and thereby be retained. After washing the column comprising sTLRR, it may be eluted. The protein fraction thus eluted may be further separated on a SDS-polyacrylamid gel and transferred on a nitrocellulose filter by a further electrophoresis. Soluble TLRR may finally be visualised according to a standard western-blotting procedure. Alternatively, it may be concentrated by centrifugation or ultrafiltration and added in this form to a consumable product in effective amounts.

In a further embodiment, the polypeptide according to the invention can be recognised by an antibody raised against the extracellular part of a TLR.

Therefore, the polypeptide according to the invention is obtainble, after immunoprecipitation, by SDS-PAGE, electroblotting to a suitable membrane and protein elution. The skilled person is well aware of these techniques.

In another embodiment, the polypeptide according to the invention exhibits, if compared to a TLR polypeptide, highest sequence similarity and/or homology to the extracellular domain of the TLR polypeptide. Preferably, the polypeptide according to the invention exhibits highest sequence similarity to the human TLR-2 molecule.

In still another embodiment, the polypeptide according to the invention is related to or a homologue of the human TLR-2 molecule.

In still a further embodiment, the polypeptide according the invention is derived from human breast milk or identical to a milk derived variant. A way of isolating the popypeptide from human milk is disclosed above.

With respect of the antibody according to an aspect of the present invention, it is clear that the skilled person is fully aware of the preparation of a monoclonal or polyclonal antibody against a specific antigen or protein. Once the protein has been isolated, an antibody may be produced according to standard techniques. An effective, polyclonal (rabbit) antibody may be produced by immunizing animals with a 20-mer peptide, syntesized artificially, mapping at the N-terminus of human TLR2 (starting 5aa from the N-terminus). Such antibodies have shown a very good reactivity with the soluble forms of TLR2.

A commercially available antibody useful for detecting sTLRR of the present invention is the anti-TLR2 polyclonal (rabbit) antibody of IMG 410, commercialized by Biocarta Europe GmbH, which was produced by immunization with a mixture of three peptides corresponding to amino acids 180-196, 353-370, 473-489 of human TLR-2.

A further antibody is anti-TLR2 polyclonal (goat) antibody TLR2 (N-17) Santa Cruz Biotechnology, Inc. Cat No: sc-8689, an antibody that works well in Western and immunoprecipitations.

Possible variations of the nucleic acid molecule intended to be included by the nucleic acid molecule of the present invention are nucleic acid molecules that hybridise, under stringent conditions, to the nucleic acid of the present invention.

The nucleic acid molecule of the present invention may further comprise an expression system wherein the expression system is capable of producing a polypeptide comprising an amino acid sequence, which has at least 50% identity with the polypeptide of the present invention.

In order to express a biologically active sTLRR, the nucleotide sequence encoding sTLRR or its functional equivalent is inserted into an appropriate expression vector, that is, a vector which contains the necessary elements for the transcription and translation of the inserted coding sequence.

Methods which are well known to those skilled in the art can be used to construct expression vectors containing a sTLRR coding sequence and appropriate transcriptional and translational controls. These methods include in vitro recombinent DNA techniques, synthetic techniques and in vivo recombinantion or genetic recombination. Such techniques are described in Sambrook et al. (1989) *Molecular Cloning, A Laboratory Manual*, Cold Spring Harbor Press, for example.

A variety of expression vector/host systems may be utilized to contain and express a sTLRR coding sequence. These include but are not limited to microorganisms such as bacteria transformed with recombinant bacteriophage, plasmid or cosmid DNA expression vectors; yeast transformed with yeast expression vectors; insect cell systems infected with virus expression vectors; plant cell systems infected with virus expression vectors or animal cell systems. In principle, all expression system that involve mammalian, bacterial, vegetal or fungal cells may be used.

Surprisingly, no functional mRNA transcript of the sTLRR was found in human mammary epithelial cells, although theoretically promising transcripts were found. In addition, it was surprisingly found that functional (soluble) variants of sTLRR may differ substantially in size (37, 40, 60, 70, and 80 kDa). These observations suggest that sTLRR is created by processing of full-length TLR2. Moreover, the fact that sTLRR interacts with antibodies raised against the extracellular part of TLR2 makes clear that sTLRR according to the present invention corresponds to the extracellular part of TLR, or a shorter fragment thereof.

Accordingly, the present invention provides the SEQ. ID. Nos 1 and 2, which correspond to the processed and soluble extracellular part of human and bovine TLR-2.

SEQ. ID. No. 1 in the sequence listing part of the present description identifies a polypeptide according to the present invention as occurring in human milk, together with shorter fragments thereof.

SEQ. ID. No. 2 in the sequence listing part of the present description identifies a polypeptide according to the present invention being the functional homologue of SEQ. ID. No 1 in *Bos taurus*. For industrial application, the functional homologue of SEQ: ID. No 2 may be more relevant, because it can be readily enriched or isolated from bovine mill in substantial amounts.

In an alternate embodiment of the invention, the coding sequence of sTLRR may be synthesized, whole or in part, using chemical methods well known in the art. Similarly, the protein itself could be produced using chemical methods to synthesize a sTLRR amino acid sequence. A possible nucleotide sequence can be deducted from the genetic code.

With respect to the polypeptide according to the present invention for use as a medicament, functional food ingredient or cosmetic, the polypeptide may be used for preventing or downregulating inflammatory conditions in a mammal.

Furthermore, the polypeptide according to the invention may be used in the prevention, prophylaxis, treatment or therapy of inflammatory conditions in a mammal.

For example, the inflammatory conditions are inflammatory conditions of the gastrointestinal tract or the skin of a mammal.

The application form of the polypeptide is not essential. For example, the polypeptide may just be consumed directly and orally after isolation and concentration as set out above. This holds true in particular if inflammatory conditions of the gastro-intestinal tract are directly treated.

If the polypeptide is used for treatment of inflammatory conditions of the skin, the sTLRR may be added to any suitable lotion, cream, balm and the like designed for treating or preventing irritations or inflammations of the skin. For example, the sTLRR may be added to oil-in-water or water-in oil emulsions. Preferably, highly concentrated sTLRR is added after emulsifying the oily and the aqueous phase. It is also possible to add sTLRR after the homogenizing step at the end. Preferably, the concentrated sTLRR is added under stirring at about 35° C. In U.S. Pat. No. 5,744,145 (NESTEC S.A.) a number of cosmetic compositions are disclosed to which sTLRR may easily be added.

The polypeptide of the present invention may further be used as a dermatological agent.

In another example, the polypeptide of the present invention may be used for prevention, prophylaxis, treatment or therapy of inflammatory conditions of muscuous membranes or mucosi of a mammal.

In addition, the polypeptide according to the invention may be used for prevention, prophylaxis, treatment or therapy of allergic reactions in a mammal.

With respect to the consumable product according to the present invention, this may be a pet food. Preferably, the consumable product is intended for human, more preferably infant consumption. It may that be a nutritional or infant formula, a chilled or shelf-stable dairy product or a confectionery.

An nutritional formula may be prepared in any suitable manner. For example, the nutritional formula may be prepared by blending together a source of dietary protein, a carbohydrate source and a fat source in appropriate proportions. If used, emulsifiers may be included in the blend. Vitamins and minerals may be added at this point but are usually added later to avoid thermal degradation. Any lipophilic vitamins, emulsifiers and the like may be dissolved into the fat source prior to blending. Water, preferably water that has been subjected to reverse osmosis, may then be mixed in to form a liquid mixture. The temperature of the water is conveniently about 50° C. to about 80° C. to aid dispersal of the ingredients. Commercially available liquefiers may be used to form the liquid mixture. The liquid mixture may then be homogenised, for example in two stages.

Purified sTLRR can be directly added in effective amounts to the liquid formula. The pH of the formula may lie between 4.5 and 7.5, which means that the protein is soluble. Of course, the allowable pH-range may be different, if the chemical properties of sTLRR have been changed, by glycosylation or by addition, deletion or replacement of amino acids, for example.

In an embodiment, a concentrated solution of sTLRR is added to a liquid (reconstituted) nutritional formula, the nutritional formula having any desired energy content. Preferably, the sTLRR is present at a final concentration of 50 ng per ml to 10 μg per ml, more preferably 100 ng to 1000 ng per ml. In the nutritional formula, the concentration may also be depending on the circumstances of the diet, in particular, whether the nutritional formula constitutes a complete diet or not. Also other circumstances may influence the final concentration of sTLRR in the formula, such as the amount of formula that is consumed, the activity of the sTLRR or the condition of the patient, for example. As a general rule, a daily dose should comprise between 10 μg to 20 mg units of the protein, preferably 100 μg to 1 mg units, depending on different conditions.

It is clear to those skilled in the art that the functions of the sTLRR polypeptide can be achieved by a variety of different amino acid sequences. Accordingly, another aspect of the invention pertains to polypeptides that contain changes in amino acid residues that are not essential for activity. Such proteins differ in amino acid sequence from the polypeptide as isolated according to the invention, yet retain biological function or activity. For example, amino acids may be substituted at "non-essential" amino acid residues. A "non-essential" amino acid residue is a residue that can be altered from the wild-type sequence of sTLRR without altering the biological function or the structural folds, whereas an "essential" amino acid residue is required for biological function. Similar functions are often complied by amino acids with a similar structural or chemical properties, for example, replacement of leucine with isoleucine. More rarely, a variant may have "non-conservative" changes, for example, replacement of glycine with tryptophan. The same holds true not only for single amino acids residues, but for entire sequences of amino acids that may be added or ommitted without altering the biological function of the protein. Hence, similar minor variations may also include amino acid deletions or insertions, or both. Very often, a short amino acid sequence within a much larger polypeptide is principally responsible for the biological activity or function of a protein.

Hence, the present invention also covers homologues of sTLRR.

The homology or sequence similarity or sequence identity of protein sequences may easily be determined according to techniques well known in the art, e.g. by using established software or computer programs, e.g. the BLAST (Basic Local Alignment Sequence Tool) program based on the work of D. Lipman and coworkers (Altschul, S. F., Gish, W., Miller, W., Myers, E. W. & Lipman, D. J. (1990) "Basic local alignment search tool." J. Mol. Biol. 215:403-410 and Altschul, S. F., Madden, T. L., Schäffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402).

BLAST® (Basic Local Alignment Search Tool) is a set of similarity search programs designed to explore all of the available sequence databases regardless of whether the query is protein or DNA. The BLAST programs have been designed for speed, with a minimal sacrifice of sensitivity to distant sequence relationships. The scores assigned in a BLAST search have a well-defined statistical interpretation, making real matches easier to distinguish from random background hits. BLAST uses a heuristic algorithm which seeks local as opposed to global alignments and is therefore able to detect relationships among sequences which share only isolated regions of similarity (Altschul, S. F., Gish, W., Miller, W., Myers, E. W. & Lipman, D. J. (1990) "Basic local alignment search tool." J. Mol. Biol. 215:403-410).

BLAST is based on modified algorithms of Smith and Waterman (Smith, T. F. & Waterman, M. S. (1981) "Identification of common molecular subsequences." J. Mol. Biol. 147:195-197) and Sellers (Sellers, P. H. (1984) "Pattern recognition in genetic sequences by mismatch density." Bull. Math. Biol. 46:501-514), to find the best segment of identity or similarity between two sequences. When using a sequence alignment program such as BLAST, to determine the degree of sequence homology, similarity or identity, the default setting may be used, or an appropriate scoring matrix, such as BLOSUM or PAM, may be selected to optimize identity, similarity or homology scores.

In order to account for artificial modifications of the amino acid sequence that may be introduced for a variety of reasons, the present invention also encompasses sequences that are not homologues but that share at least a sequence similarity as defined below or the three-dimensional structure or the function of the protein according to the present invention.

In an embodiment, the polypeptide according to the present invention comprises an amino acid sequence which is at least about 50%, 55%, 60%, 65%, 70%, 75%, 85%, 90%, 95%, 98% or more similar to the protein according to the present invention.

The present invention also comprises nucleotide sequences, that is DNA or RNA, encoding these amino acid sequences.

In an embodiment, the polypeptide according to the invention is a fusion protein, for example for screening of peptide libraries for inhibitors of sTLRR activity or to make it recognizable by a commercially available antibody. A fusion protein may also be engineered to contain a cleavage site located between a sTLRR sequence and the heterologuous protein sequence, so that the sTLRR may be cleaved and purified away from the heterologuous moiety.

The effective soluble polypeptide according to the present invention may also be a dimer, trimer etc. It may be a homo- or a heterodimer, -trimer, -polymer. For examples, the different domains of the effective polypeptide are covalently linked by one or more disulfide bonds. Especially in extracellular proteins or extracellular domains disulfide bonds within different proteins or within the same proteins are often found. The present invention therefore includes the possibility that two identical or different polypeptide chains are linked to each other to form a homo- or a heterodimer or polymer. It is also possible that two very similar domains that vary only in a limited number of amino acid residues or that are differently glycosylated form a hetero- or homodimer. In all these cases, the present invention comprises proteins or multi-domain proteins that comprise at least one domain having the features according to the present invention.

It will be appreciated by those skilled in the art that as a result of the degeneracy of the genetic code, a multitude of sTLRR-encoding nucleotide sequences, some bearing minimal similarity to the nucleotide sequences of any known and naturally occurring gene may be produced. The invention contemplates each and every possible variation of nucleotide sequence that could be made by selecting combinations based on possible codon choices. Those combinations are made in accordance with the standard triplet genetic code as applied to the nucleotide sequence of naturally occurring sTLRR, and all such variations are to be considered as being specifically disclosed.

The nucleotide sequence according to the present invention can be engineered in order to alter a sTLRR coding sequence for a variety of reasons, including but not limited to, alterations which modify the cloning, processing and/or expression of the gene product. For example, mutations may be introduced using techniques which are well known in the art, for example, site-directed mutagenesis to insert new restriction sites, to alter glycosylation patterns, to change codon preferences, to produce splice variants, etc. Hence, in an embodiment of the present invention, a nucleic acid molecule is concerned that shares at least, 50%, 55%, 60%, 65%, 70%, 75%, 80%, 85%, 90%, 95%, 97%, 99% or more of homology with the sequences encoding the protein according to the present invention.

The sequence of the protein according to the present invention also covers sequences that only partly comprise the sequence encoding the protein according to the present invention.

Its solubility under physiological conditions and at the same time its relevance in innate immune responses make sTLRR a precious tool in a huge number of pathogenic-or non pathogenic conditions. For example, sTLRR may be used for diagnostic purposes, exploiting its ability to bind to bacterial epitopes or antigens. In this aspect, the significance of sTLRR is similar to that of antibodies. Hence sTLRR may be particularly useful in the development of novel diagnostic targets or therapeutic agents to regulate immune or inflammatory response. For example, conditions relating to dysregulation of an immune response, such as autoimmune diseases, inflammatory bowel diseases or allergy including asthma.

The following examples are given by way of illustration only and in no way should be construed as limiting the subject matter of the present application. Percentages and parts are by weight unless otherwise indicated.

EXAMPLES

Example 1

Detection of Soluble TLR-2 in Human Breast Milk

Methods

Human milk samples, taken at different days post partum (0, 5, 6, 8) were diluted 1:150 with Laemmli reducing sample buffer, electrophoresed on 10% SDS-PAGE (Mini-Protean II, BioRad) and analysed by Western blotting, as previously described (Durieux, J. J., N. Vita, O. Popescu, F. Guette, J. Calzada-Wack, R. Munker, R. E, Schmidt, J. Lupker, P. Ferrara, H. W. Ziegler-Heitbrock, and M. O. Labeta. 1994, The two soluble forms of the lipopolysaccharide receptor, CD14: characterization and release by normal human monocytes. Eur. J. Immunol. 24: 2006-2012.), by using a TLR-2 specific antibody (purified goat polyclonal antibody, Santa Cruz) or normal goat IgG (Santa Cruz) diluted 1:2000 (100 ng/ml) with phosphate-buffered saline pH 7.4 (PBS) supplemented with 2% (w/v) BSA and 0.1% (v/v) Tween-20. The anti TLR-2 antibody recognises a 17-amino acid peptide mapping near the N-terminus of the TLR-2 polypeptide. Detection was carried out with a horseradish peroxidase-conjugated anti goat antibody (Santa Cruz), diluted 1:4000 with PBS supplemented with 0.5% (w/v) BSA and 0.1% (v/v) Tween-20, by the enhanced chemiluminescence method (ECL, Amersham) following the manufacturer's instructions. To confirm the specificity of the anti TLR-2 Western blots, in some experiments and before blotting, the anti TLR-2 antibody was preincubated (2h/room temperature) with 10 time excess concentration of the peptide (Santa Cruz) used to raise the anti TLR-2 antibody.

Additionally, the concentration of soluble CD14 (described ion) was determined for each sample. (Human breast milk was collected from healthy donors after written consent). Milk was processed within 2 hours after collection. After centrifugation the cellular pellet was kept for other analysis and the supernatant was frozen at −80° C. until testing sCD14 by ELISA (Immuno-Biological Laboratories). The examined samples showed a sCD14 concentration ranging between 26 and 81 µg per ml.

Results and Conclusion

Figure 2:
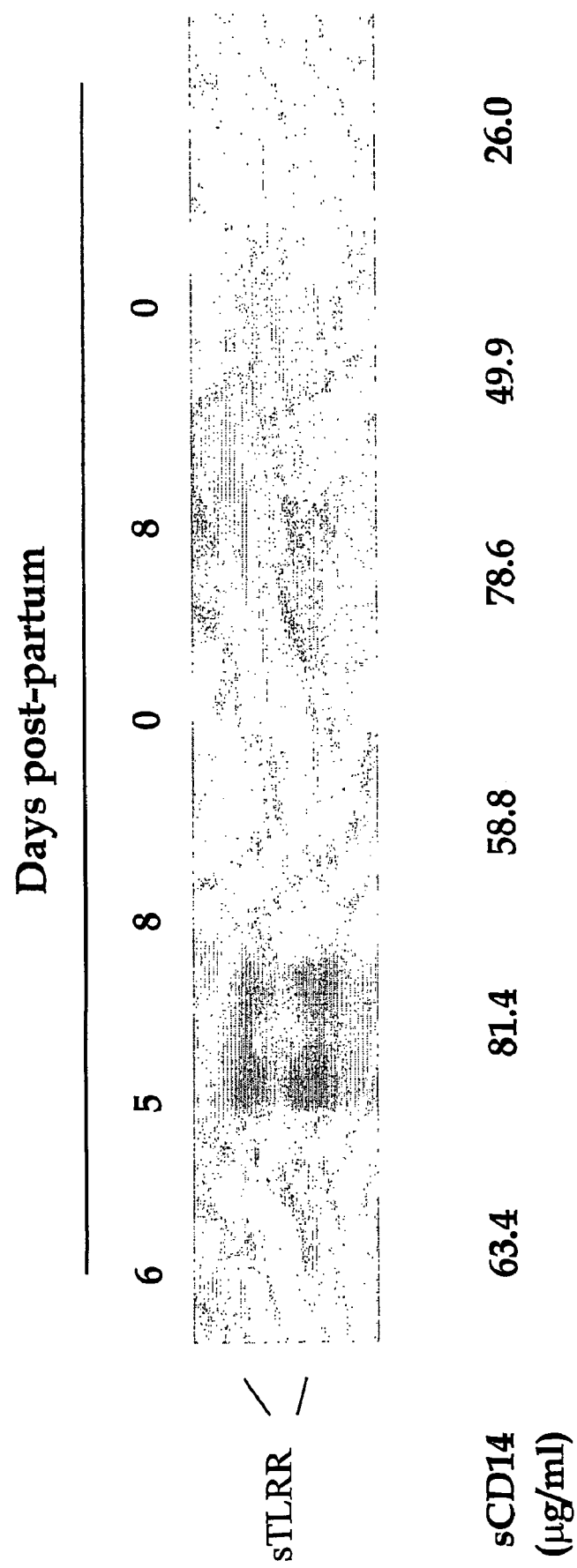
FIG. 2 shows a Western blot analysis of human milk fractions collected at different days post partum of sTLRR as set out above (corresponding to scheme FIG. 1, lanes 1 and 2). The figure also shows sCD14 concentrations that were determined in parallel to the sTLRR analysis.

The result of the western blotting experiments are shown in FIGS. 1 and 2, revealing two bands of 38 and 40 kDa, where the anti TLR-2 antibody was used (lanes 1 and 2 of FIG. 1).

The novel polypeptide was not detected when the membranes were blotted with the anti TLR-2 antibody preincubated with the specific 17-aa TLR2 peptide, which was used to raise the antibody (lanes 3 and 4 of FIG. 1).

The expression of sTLRR was higher at earlier times post partum (day 0 to day 5). Notably, also a direct correlation between the expression of sTLRR and the concentration of milk sCD 14 was found (FIG. 2). Furthermore, expression level comparisons between sTLRR and sCD14 in milk suggested that sTLRR is expressed at approximately 6-7 times lower levels than sCD14.

In conclusion, sTLRR is a novel polypeptide occurring in human breast milk, which is a soluble homologue of human TLR2. The function of sTLRR is probably linked to the one of sCD14, which makes sTLRR a candidate for a regulatory of inflammatory conditions. In addition this may represent a molecule to preserve the homeostasis of the intestinal mucosa upon the permanent pro-inflammatory challenge of bacteria and bacterial products.

Example 2

Purification of sTLRR

Significant amounts of highly purified sTLRR for further studies may be obtained by immunoprecipitation followed by SDS-PAGE, electroblotting to PVDF membranes, and protein elution.

Methods

Typically, 1 ml of human breast milk (preferably colostrum, day 1 to 5 postpartum) is diluted 1:10 with a diluting buffer consisting of 50 mM Tris/HCl, 150 mM NaCl, pH7.4 buffer, supplemented with 0.5% (w/v) NP-40 (BDH), 1 mM PMSF, 1 µg/ml leupeptin, 1 µg/ml pepstatin, 1 mM EDTA, and 50 mM NaF (all protease inhibitors from Sigma). The diluted sample is pre-cleared by incubation (1 h, 4 ,C with rotation) with 30 µg normal goat IgG (Santa Cruz) followed by two sequential incubations with 250 µl of Protein G-Sepharose (1:1 slurry; Sigma), the last incubation is extended overnight. Each round of Protein G-Sepharose incubation is followed by pelleting the beads by gentle centrifugation (800 g, 2 min at 4° C.), and the beads are discarded. The pre-cleared and diluted milk sample is incubated (1 h, 4° C. with rotation) with 30 µg of polyclonal (goat) anti TLR-2 antibody (Santa Cruz) followed by 150 µl of Protein G-Sepharose. Following gentle centrifugation the Sepharose beads, the supernatant is discarded and the pellet washed five times with the diluting buffer. Subsequently, the beads are resuspended in 100 µl of Laemmli reducing sample buffer, boiled (5 min.), and the eluted material is loaded onto a 10% SDS-polyacrylamide gel. Following electrophoresis, the immunoprecipitated molecule is transferred to a PVDF membrane and eluted by acidic extraction following standard protocols (Current Protocols in Protein Science, J. Coligan et al. eds.; J. Wiley & Sons; chapter 10, section 10.7). Alternatively, for mass spectrometric analysis, the protein is digested in-gel with Trypsin (sequence grade; Promega) in preparation for the analysis, as described (Current Protocols in Protein Science, J. Coligan et al. eds.; J. Wiley & Sons; chapter 16, supplement 14, section 4).

Conclusion

The novel polypeptide, sTLRR, is obtained in an isolated form. Approximately, the concentration of the polypeptide in the elution is in the range of 0.5 to 3 µg, preferably 1-2 µg per ml.

Example 3

Co-immunoprecipitation of sTLRR and sCD14

Method and Results

It was tested if sTLRR interacts with sCD14 in human milk. A strong 48-kDa polypeptide band was detected with a sCD14 specific polyclonal antibody (rabbit) by western blot of milk samples following immunoprecipitation with an anti TLR2 goat polyclonal antibody, but not with the control goat IgG.

Stripping and reprobing the membranes with anti TLR2 antibody confirmed the presence of the 38 and 40 kDa polypeptide, in addition to the 48-kDa sCD14 band. This 80-kDa band was detectable when reprobing the membrane with the anti TLR2 specific antibody, but not with control Ig.

Conclusion

There is evidence that the novel polypeptide (sTLRR) interacts or binds to the previously described sCD14 and forms a 80-kDa complex. The function of the complex must be tightly linked to the functions of sCD14, previously described (Frey E A, Miller D S, Gullstein Jahr T, Sundan A, Bazil V, Espevik T, Finlay B B, Wright S D. Soluble CD14 participates in the response of cells to lipopolysaccharide. J. Exp. Med. 1992, 176: 1665-1671).

Example 4

Expression and its Modification of sTLRR by Mammary Epithelial Cells

This experiment aims at identifying the source of the novel sTLRR polypeptide.

Method and Results

Immunoprecipitation followed by Western blotting with anti TLR2 specific antibody showed expression of the 38 and 40 kDa TLRR polypeptides as well as the 80 kDa band in the culture supernatants and total lysates of the mammary epithelial cell line MCF-7.

Furthemore, it was tested to modify the expression of sTLRR by using different stimuli including, the estrogen mimmetic phenyl red, synthetic lipopeptide, INF-γ/TNF-α, LPS and PMA/Ionomycin. Phenyl red and INF-γ/TNF-α induced a significant up-modulation of both, the 38/40 kDa and 80 kDa molecules in the total lysate as well as in the culture supernatant.

Conclusion

In conclusion, the novel polypeptide (sTLRR) acts as an immunomodulatory agent. In particular, it downregulates an immune response by inhibiting the induction of pro-inflammatory cytokines. Hence, the novel polypeptide has a potential for regulating various diseases linked to immune system overreactions, as, for example, allergies, inflammatory diseases of the gut, systemic chronic inflammations and autoimmune diseases.

Example 5

Nutritional Formula Comprising sTLRR

In order to downregulate an inflammatory innate immune response in the gastro-intestinal tract of children, a nutritional formula is prepared comprising sTLRR in effective amounts.

Soluble TLRR prepared in enriched form as disclosed above is added to nutritionally balanced product comprising about 15% of dry matter in such a quantity that the preparation thus obtained comprises an amount of about 0.1 to 100, preferably 0.5 to 50 µg of sTLRR per g of dry matter. The dry matter consists of 20% protein, 45% carbohydrate, 32.3% fat and 2.7% minerals and vitamins according to recommended values. This nutritional formula has an energy content of about 75 kcal/dl (315 kJ/dl).

Example 6

Further Effects of the sTLRR

Methods

To test the regulatory effect of sTLLR, anti TLR2 Antibodies were added prior to cell stimulation by LPS, U373 astrocytoma cells (ATCC) were cultured and activated with E. coli LPS (100 ng/ml) in medium containing 2% human breast milk (1 to 5 days postpartum) as previously described (Labeta M O, Vidal K, Rey nores J A, Arias M, Vita N, Morgan B P, Guillemot J C, Loyaux D, Ferrara P, Schmid D, Affolter M, Borysiewicz L K, Donnet-Hughes A, Schiffrin E J. Innate recognition of bacteria in human milk is mediated by a milk-derived highly expressed pattern recognition receptor, soluble CD14, J. Exp. Med. 2000, 191: 1807-1812). Prior to cell stimulation, the milk-containing medium was preincubated (30 min/ice) with the anti TLR2 Abs (10 micrograms/ml) or an isotype-matched control. After 24 h incubation, culture supernatants were tested for IL-6 release by ELISA. Cell aliquots were taken after 4 h following stimulation and tested for CD54 (ICAM-1) cell surface expression by flow cytometry.

Results and Conclusion

The use of anti-TLR2 in the preincubation of cells enhanced singnificantly the LPS-induced milk—mediated expression of ICAM-1 (CD54) and secretion of IL-6 by the cell lines. The extent of the enhancing effect for several experiments was in average of 100% for IL-6 release and 100% for CD-54. The enhancing effect was also detected when purified sCD14 was used instead of milk. This indicates that the sTLRR molecule modulatory activity takes place, at least in some cases, when complexed with the sCD14 molecule.

The anti-TLR2 present in milk and also in any other body fluid seems to be an important regulatory molecule of bacterial activation of innate and subsequently adaptive immune responses. This may be of crucial importance in the control of an exaggerated inflammatory response to bacterial products in the neonatal period when the host encounters for the first time a plethora of new bacterial antigens and pro-inflammatory molecules.

Example 7

Different Fragments of sTLRR Isolated from Human Milk

Western blot analysis of milk samples diluted 1:50 with Laemmli reducing sample buffer, separated by 10% SDS-PAGE, and immunoblotted with anti-TLR2 polyclonal (goat) antibody (sc 8689, Santa Cruz, Calif., USA) raised against a 17-amino acid peptide mapping to the N-terminus of the human TLR2 protein. Blots were visualized by incubation with a donkey anti-goat IgG-peroxidase conjugated Ab follwed by enhanced chemiluminiscence (Amersham). For details see Example 1.

Figure 3:
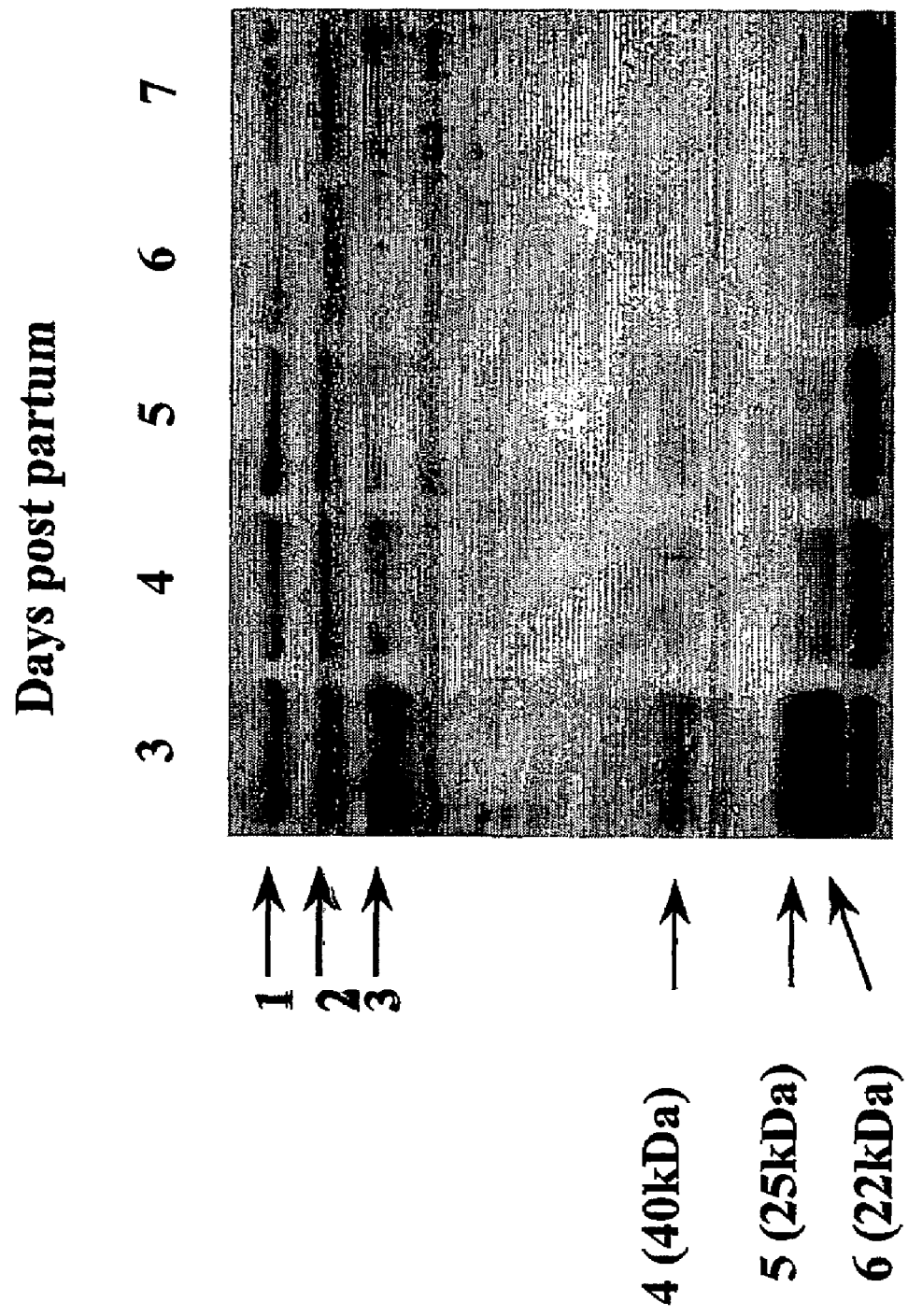
FIG. 3 shows a Western blot analysis of human milk fractions collected at different days post partum. An anti-TLR2 polyclonal (goat) antibody (sc 8689, Santa Cruz, Calif., USA) raised against a 17-amino acid peptide mapping to the N-terminus of the human TLR2 protein was used for the immunoblotting. The fragments of sTLRR and their sizes are: 1 (80 kDa), 2 (70 kDa), 3 (60 kDa), 4 (40 kDa), 5 (25 kDa), and 6 (22 kDa) (Example 7).

The results are depicted in FIG. 3, where different fractions of sTLRR, which correspond to fragments of SQ ID No. 1 can be seen. The fragments and their sizes are: 1 (80 kDa), 2 (70 kDa), 3 (60 kDa), 4 (40 kDa), 5 (25 kDa), and 6 (22 kDa).

The invention claimed is:

1. An isolated polypeptide having a molecular weight of from about 22 kDa to about 80 kDa as measured by SDS PAGE and which has 95% or more amino acid similarity to a sequence selected from the group consisting of SEQ ID NO:1 and SEQ ID NO:2, wherein said polypeptide is a naturally occurring truncated form of the full length toll-like receptor 2 protein, wherein said polypeptide binds bacterial lipopeptide.

2. The isolated polypeptide according to claim 1, having a molecular weight of about 22, 25, 38, 40, 60, 70 or 80 kDa as measured by SDS PAGE.

3. The isolated polypeptide according to claim 1, which is obtainable by immunoprecipitation of mammalian fluids, conducted with an anti TLR2 antibody.

4. An isolated nucleic acid molecule having a nucleotide sequence encoding a polypeptide having a molecular weight of from about 22 kDa to about 80 kDa as measured by SDS PAGE and which has 95% or more amino acid similarity to a sequence selected from the group consisting of SEQ ID NO:1 and SEQ ID NO:2, wherein said nucleic acid molecule encodes a naturally occurring truncated form of the full length toll-like receptor 2 protein that binds bacterial lipopeptide.

5. A composition including a polypeptide having a molecular weight of from about 22 kDa to about 80 kDa as measured by SDS PAGE and which has 95% or more amino acid similarity to a sequence selected from the group consisting of SEQ ID NO:1 and SEQ ID NO:2, wherein said nucleic acid molecule encodes a naturally occurring truncated form of the full length toll-like receptor 2 protein that binds bacterial lipopeptide and a pharmaceutical excipient.

* * * * *

SEQUENCE LISTING

```
<160> NUMBER OF SEQ ID NOS: 2

<210> SEQ ID NO 1
<211> LENGTH: 570
<212> TYPE: PRT
<213> ORGANISM: Homo sapiens

<400> SEQUENCE: 1

Lys Glu Glu Ser Ser Asn Gln Ala Ser Leu Ser Cys Asp Arg Asn Gly
1               5                   10                  15

Ile Cys Lys Gly Ser Ser Gly Ser Leu Asn Ser Ile Pro Ser Gly Leu
            20                  25                  30

Thr Glu Ala Val Lys Ser Leu Asp Leu Ser Asn Asn Arg Ile Thr Tyr
        35                  40                  45
```

-continued

```
Ile Ser Asn Ser Asp Leu Gln Arg Cys Val Asn Leu Gln Ala Leu Val
 50                  55                  60
Leu Thr Ser Asn Gly Ile Asn Thr Ile Glu Glu Asp Ser Phe Ser Ser
 65                  70                  75                  80
Leu Gly Ser Leu Glu His Leu Asp Leu Ser Tyr Asn Tyr Leu Ser Asn
                     85                  90                  95
Leu Ser Ser Ser Trp Phe Lys Pro Leu Ser Ser Leu Thr Phe Leu Asn
                100                 105                 110
Leu Leu Gly Asn Pro Tyr Lys Thr Leu Gly Glu Thr Ser Leu Phe Ser
                115                 120                 125
His Leu Thr Lys Leu Gln Ile Leu Arg Val Gly Asn Met Asp Thr Phe
130                 135                 140
Thr Lys Ile Gln Arg Lys Asp Phe Ala Gly Leu Thr Phe Leu Glu Glu
145                 150                 155                 160
Leu Glu Ile Asp Ala Ser Asp Leu Gln Ser Tyr Glu Pro Lys Ser Leu
                165                 170                 175
Lys Ser Ile Gln Asn Val Ser His Leu Ile Leu His Met Lys Gln His
                180                 185                 190
Ile Leu Leu Leu Glu Ile Phe Val Asp Val Thr Ser Ser Val Glu Cys
                195                 200                 205
Leu Glu Leu Arg Asp Thr Asp Leu Asp Thr Phe His Phe Ser Glu Leu
210                 215                 220
Ser Thr Gly Glu Thr Asn Ser Leu Ile Lys Lys Phe Thr Phe Arg Asn
225                 230                 235                 240
Val Lys Ile Thr Asp Glu Ser Leu Phe Gln Val Met Lys Leu Leu Asn
                245                 250                 255
Gln Ile Ser Gly Leu Leu Glu Leu Glu Phe Asp Asp Cys Thr Leu Asn
                260                 265                 270
Gly Val Gly Asn Phe Arg Ala Ser Asp Asn Asp Arg Val Ile Asp Pro
                275                 280                 285
Gly Lys Val Glu Thr Leu Thr Ile Arg Arg Leu His Ile Pro Arg Phe
290                 295                 300
Tyr Leu Phe Tyr Asp Leu Ser Thr Leu Tyr Ser Leu Thr Glu Arg Val
305                 310                 315                 320
Lys Arg Ile Thr Val Glu Asn Ser Lys Val Phe Leu Val Pro Cys Leu
                325                 330                 335
Leu Ser Gln His Leu Lys Ser Leu Glu Tyr Leu Asp Leu Ser Glu Asn
                340                 345                 350
Leu Met Val Glu Glu Tyr Leu Lys Asn Ser Ala Cys Glu Asp Ala Trp
                355                 360                 365
Pro Ser Leu Gln Thr Leu Ile Leu Arg Gln Asn His Leu Ala Ser Leu
370                 375                 380
Glu Lys Thr Gly Glu Thr Leu Leu Thr Leu Lys Asn Leu Thr Asn Ile
385                 390                 395                 400
Asp Ile Ser Lys Asn Ser Phe His Ser Met Pro Glu Thr Cys Gln Trp
                405                 410                 415
Pro Glu Lys Met Lys Tyr Leu Asn Leu Ser Ser Thr Arg Ile His Ser
                420                 425                 430
Val Thr Gly Cys Ile Pro Lys Thr Leu Glu Ile Leu Asp Val Ser Asn
                435                 440                 445
Asn Asn Leu Asn Leu Phe Ser Leu Asn Leu Pro Gln Leu Lys Glu Leu
450                 455                 460
Tyr Ile Ser Arg Asn Lys Leu Met Thr Leu Pro Asp Ala Ser Leu Leu
```

-continued

```
                465                 470                 475                 480

Pro Met Leu Leu Val Leu Lys Ile Ser Arg Asn Ala Ile Thr Thr Phe
                485                 490                 495

Ser Lys Glu Gln Leu Asp Ser Phe His Thr Leu Lys Thr Leu Glu Ala
            500                 505                 510

Gly Gly Asn Asn Phe Ile Cys Ser Cys Glu Phe Leu Ser Phe Thr Gln
            515                 520                 525

Glu Gln Gln Ala Leu Ala Lys Val Leu Ile Asp Trp Pro Ala Asn Tyr
            530                 535                 540

Leu Cys Asp Ser Pro Ser His Val Arg Gly Gln Gln Val Gln Asp Val
545                 550                 555                 560

Arg Leu Ser Val Ser Glu Cys His Arg Thr
            565                 570

<210> SEQ ID NO 2
<211> LENGTH: 567
<212> TYPE: PRT
<213> ORGANISM: Bos taurus

<400> SEQUENCE: 2

Ala Ser Asp Gln Ala Ser Ser Leu Ser Cys Asp Pro Thr Gly Val Cys
1               5                   10                  15

Asp Gly His Ser Arg Ser Leu Asn Ser Ile Pro Ser Gly Leu Thr Ala
            20                  25                  30

Gly Val Lys Ser Leu Asp Leu Ser Asn Asn Asp Ile Thr Tyr Val Gly
        35                  40                  45

Asn Arg Asp Leu Gln Arg Cys Val Asn Leu Lys Thr Leu Arg Leu Gly
    50                  55                  60

Ala Asn Glu Ile His Thr Val Glu Glu Asp Ser Phe Phe His Leu Arg
65                  70                  75                  80

Asn Leu Glu Tyr Leu Asp Leu Ser Tyr Asn Arg Leu Ser Asn Leu Ser
                85                  90                  95

Ser Ser Trp Phe Arg Ser Leu Tyr Val Leu Lys Phe Leu Asn Leu Leu
            100                 105                 110

Gly Asn Leu Tyr Lys Thr Leu Gly Glu Thr Ser Leu Phe Ser His Leu
        115                 120                 125

Pro Asn Leu Arg Thr Leu Lys Val Gly Asn Ser Asn Phe Thr Glu
    130                 135                 140

Ile His Glu Lys Asp Phe Thr Gly Leu Thr Phe Leu Glu Glu Leu Glu
145                 150                 155                 160

Ile Ser Ala Gln Asn Leu Gln Ile Tyr Val Pro Lys Ser Leu Lys Ser
                165                 170                 175

Ile Gln Asn Ile Ser His Leu Ile Leu His Leu Lys Gln Pro Ile Leu
            180                 185                 190

Leu Val Asp Ile Leu Val Asp Ile Val Ser Ser Leu Asp Cys Phe Glu
        195                 200                 205

Leu Arg Asp Thr Asn Leu His Thr Phe His Phe Ser Glu Ala Ser Ile
    210                 215                 220

Ser Glu Met Ser Thr Ser Val Lys Lys Leu Ile Phe Arg Asn Val Gln
225                 230                 235                 240

Phe Thr Asp Glu Ser Phe Val Glu Val Lys Leu Phe Asn Tyr Val
                245                 250                 255

Ser Gly Ile Leu Glu Val Glu Phe Asp Asp Cys Thr His Asp Gly Ile
            260                 265                 270
```

-continued

```
Gly Asp Phe Arg Ala Leu Ser Leu Asp Arg Ile Arg His Leu Gly Asn
        275                 280                 285

Val Glu Thr Leu Thr Ile Arg Lys Leu His Ile Pro Gln Phe Phe Leu
        290                 295                 300

Phe His Asp Leu Ser Ser Ile Tyr Pro Leu Thr Gly Arg Val Lys Arg
305                 310                 315                 320

Val Thr Ile Glu Asn Ser Lys Val Phe Leu Val Pro Cys Leu Leu Ser
                325                 330                 335

Gln His Leu Lys Ser Leu Glu Tyr Leu Asp Leu Ser Glu Asn Leu Met
                340                 345                 350

Ser Glu Glu Thr Leu Lys Asn Ser Ala Cys Lys Asp Ala Trp Pro Phe
        355                 360                 365

Leu Gln Thr Leu Val Leu Arg Gln Asn Arg Leu Lys Ser Leu Glu Lys
        370                 375                 380

Thr Gly Glu Leu Leu Leu Thr Leu Glu Asn Leu Asn Asn Leu Asp Ile
385                 390                 395                 400

Ser Lys Asn Asn Phe Leu Ser Met Pro Glu Thr Cys Gln Trp Pro Gly
                405                 410                 415

Lys Met Lys Gln Leu Asn Leu Ser Ser Thr Arg Ile His Ser Leu Thr
                420                 425                 430

Gln Cys Leu Pro Gln Thr Leu Glu Ile Leu Asp Val Ser Asn Asn Asn
        435                 440                 445

Leu Asp Ser Phe Ser Leu Ile Leu Pro Gln Leu Lys Glu Leu Tyr Ile
        450                 455                 460

Ser Arg Asn Lys Leu Lys Thr Leu Pro Asp Ala Ser Phe Leu Pro Val
465                 470                 475                 480

Leu Ser Val Met Arg Ile Ser Arg Asn Ile Ile Asn Thr Phe Ser Lys
                485                 490                 495

Glu Gln Leu Asp Ser Phe Gln Gln Leu Lys Thr Leu Glu Ala Gly Gly
                500                 505                 510

Asn Asn Phe Ile Cys Ser Cys Asp Phe Leu Ser Phe Thr Gln Gly Gln
        515                 520                 525

Gln Ala Leu Gly Arg Val Leu Val Asp Trp Pro Asp Asp Tyr Arg Cys
        530                 535                 540

Asp Ser Pro Ser His Val Arg Gly Gln Arg Val Gln Asp Ala Arg Leu
545                 550                 555                 560

Ser Leu Ser Glu Cys His Arg
                565
```